(12) United States Patent  
Kerr et al.

(10) Patent No.: US 9,192,433 B2  
(45) Date of Patent: *Nov. 24, 2015

(54) APPARATUS FOR PERFORMING AN ELECTROSURGICAL PROCEDURE

(71) Applicant: COVIDIEN LP, Mansfield, MA (US)

(72) Inventors: Duane E. Kerr, Loveland, CO (US); Glenn A. Horner, Boulder, CO (US)

(73) Assignee: Covidien LP, Mansfield, MA (US)

( * ) Notice: Subject to any disclaimer, the term of this patent is extended or adjusted under 35 U.S.C. 154(b) by 256 days.

This patent is subject to a terminal disclaimer.

(21) Appl. No.: 13/947,991

(22) Filed: Jul. 22, 2013

(65) Prior Publication Data

US 2013/0310832 A1   Nov. 21, 2013

Related U.S. Application Data

(63) Continuation of application No. 12/792,001, filed on Jun. 2, 2010, now Pat. No. 8,491,624.

(51) Int. Cl.
*A61B 18/14* (2006.01)
*A61B 17/29* (2006.01)
*A61B 18/00* (2006.01)

(52) U.S. Cl.
CPC .............. *A61B 18/1445* (2013.01); *A61B 17/29* (2013.01); *A61B 2017/2936* (2013.01); *A61B 2018/0063* (2013.01); *A61B 2018/00083* (2013.01); *A61B 2018/00589* (2013.01);
(Continued)

(58) Field of Classification Search
CPC ............... A61B 2017/2933; A61B 2017/2936; A61B 2017/2926; A61B 2017/2939; A61B 2017/2825; A61B 17/29; Y10T 29/49002
USPC ...................................... 606/205–207, 51, 52
See application file for complete search history.

(56) References Cited

U.S. PATENT DOCUMENTS

| | | |
|---|---|---|
| 3,503,396 A | 3/1970 | Pierie et al. |
| 3,895,636 A | 7/1975 | Schmidt |
| D249,549 S | 9/1978 | Pike |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

Australian Examination Report dated May 14, 2015 issued in Australian Appln. No. 2013205387.

(Continued)

*Primary Examiner* — Michael Peffley

(57) ABSTRACT

A surgical instrument is provided and includes a housing having a shaft. An end effector assembly operatively connects to the shaft and has a pair of first and second jaw members. A jaw insert is operably associated with the first and second jaw members. The jaw insert includes one or more cam slots defined therein configured to receive a cam pin that upon movement thereof rotates the first and second jaw members from an open position to a clamping position and an opening defined therein configured to securely house a pivot pin that provides a point of pivot for the first and second jaw members. The jaw insert is manufactured from an insulative medium to dielectrically isolate the first and second jaw members.

13 Claims, 8 Drawing Sheets

(52) U.S. Cl.
CPC ............... *A61B2018/00595* (2013.01); *A61B 2018/00601* (2013.01); *Y10T 29/49002* (2015.01)

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,250,056 A | 10/1993 | Hasson | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,454,378 A | 10/1995 | Palmer et al. | |
| 5,454,819 A | 10/1995 | Knoepfler | |
| 5,591,182 A | 1/1997 | Johnson | |
| 5,637,111 A * | 6/1997 | Sutcu et al. | 606/51 |
| D384,413 S | 9/1997 | Zlock et al. | |
| 5,697,949 A * | 12/1997 | Giurtino et al. | 606/205 |
| 5,746,759 A | 5/1998 | Meade et al. | |
| H1745 H | 8/1998 | Paraschac | |
| 5,833,695 A | 11/1998 | Yoon | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,743,230 B2 * | 6/2004 | Lutze et al. | 606/51 |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 7,063,699 B2 | 6/2006 | Hess et al. | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,766,910 B2 * | 8/2010 | Hixson et al. | 606/51 |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,887,536 B2 | 2/2011 | Johnson | |
| 7,918,848 B2 | 4/2011 | Lau | |
| 7,951,150 B2 | 5/2011 | Johnson | |
| 8,016,827 B2 | 9/2011 | Chojin | |
| D649,249 S | 11/2011 | Guerra | |
| D649,643 S | 11/2011 | Allen, IV et al. | |
| 8,112,871 B2 | 2/2012 | Brandt | |
| 8,133,254 B2 | 3/2012 | Dumbauld | |
| 8,142,473 B2 | 3/2012 | Cunningham | |
| 8,162,965 B2 | 4/2012 | Reschke | |
| 8,187,273 B2 | 5/2012 | Kerr | |
| D661,394 S | 6/2012 | Romero et al. | |
| 8,197,479 B2 | 6/2012 | Olson | |
| 8,226,650 B2 | 7/2012 | Kerr | |
| 8,251,994 B2 | 8/2012 | McKenna | |
| 8,266,783 B2 | 9/2012 | Brandt | |
| 8,277,446 B2 | 10/2012 | Heard | |
| 8,277,447 B2 | 10/2012 | Garrison | |
| 8,282,634 B2 | 10/2012 | Cunningham | |
| 8,287,536 B2 | 10/2012 | Mueller | |
| 8,292,886 B2 | 10/2012 | Kerr | |
| 2006/0020287 A1 | 1/2006 | Lee et al. | |
| 2006/0079933 A1 | 4/2006 | Hushka et al. | |
| 2006/0217697 A1 | 9/2006 | Lau et al. | |
| 2007/0173814 A1 | 7/2007 | Hixson et al. | |
| 2007/0260242 A1 | 11/2007 | Dycus et al. | |
| 2010/0023009 A1 | 1/2010 | Moses | |
| 2010/0042140 A1 | 2/2010 | Cunningham | |
| 2010/0042143 A1 | 2/2010 | Cunningham | |
| 2010/0087816 A1 | 4/2010 | Roy | |
| 2010/0094271 A1 | 4/2010 | Ward | |
| 2010/0094287 A1 | 4/2010 | Cunningham | |
| 2010/0100122 A1 | 4/2010 | Hinton | |
| 2010/0130971 A1 | 5/2010 | Baily | |
| 2010/0179543 A1 | 7/2010 | Johnson | |
| 2010/0179545 A1 | 7/2010 | Twomey | |
| 2010/0179546 A1 | 7/2010 | Cunningham | |
| 2010/0249769 A1 | 9/2010 | Nau, Jr. | |
| 2010/0280511 A1 | 11/2010 | Rachlin | |
| 2011/0015632 A1 | 1/2011 | Artale | |
| 2011/0034918 A1 | 2/2011 | Reschke | |
| 2011/0046623 A1 | 2/2011 | Reschke | |
| 2011/0054468 A1 | 3/2011 | Dycus | |
| 2011/0054469 A1 | 3/2011 | Kappus | |
| 2011/0054471 A1 | 3/2011 | Gerhardt | |
| 2011/0054472 A1 | 3/2011 | Romero | |
| 2011/0060333 A1 | 3/2011 | Mueller | |
| 2011/0060334 A1 | 3/2011 | Brandt | |
| 2011/0060335 A1 | 3/2011 | Harper | |
| 2011/0071523 A1 | 3/2011 | Dickhans | |
| 2011/0077648 A1 | 3/2011 | Lee | |
| 2011/0077649 A1 | 3/2011 | Kingsley | |
| 2011/0082494 A1 | 4/2011 | Kerr | |
| 2011/0087221 A1 | 4/2011 | Siebrecht | |
| 2011/0098689 A1 | 4/2011 | Nau, Jr. | |
| 2011/0118736 A1 | 5/2011 | Harper | |
| 2011/0184405 A1 | 7/2011 | Mueller | |
| 2011/0190653 A1 | 8/2011 | Harper | |
| 2011/0190765 A1 | 8/2011 | Chojin | |
| 2011/0193608 A1 | 8/2011 | Krapohl | |
| 2011/0218530 A1 | 9/2011 | Reschke | |
| 2011/0230880 A1 | 9/2011 | Chojin | |
| 2011/0238066 A1 | 9/2011 | Olson | |
| 2012/0183654 A1 | 7/2012 | Zorich | |
| 2013/0185922 A1 | 7/2013 | Twomey | |
| 2013/0190753 A1 | 7/2013 | Garrison | |
| 2013/0190755 A1 | 7/2013 | Deborski | |
| 2013/0190760 A1 | 7/2013 | Allen, IV | |
| 2013/0197503 A1 | 8/2013 | Orszulak | |
| 2013/0218198 A1 | 8/2013 | Larson | |
| 2013/0218199 A1 | 8/2013 | Kerr | |
| 2013/0219691 A1 | 8/2013 | Reschke | |
| 2013/0226177 A1 | 8/2013 | Brandt | |
| 2013/0226178 A1 | 8/2013 | Brandt | |

(56) References Cited

U.S. PATENT DOCUMENTS

| | | | |
|---|---|---|---|
| 2013/0226226 | A1 | 8/2013 | Garrison |
| 2013/0232753 | A1 | 9/2013 | Ackley |
| 2013/0238016 | A1 | 9/2013 | Garrison |
| 2013/0245623 | A1 | 9/2013 | Twomey |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19606716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1177771 | 2/2002 |
| EP | 1777771 | 2/2002 |
| JP | 61-501068 | 9/1984 |
| JP | 65-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-511401 | 12/1994 |
| JP | 06343644 | 12/1994 |
| JP | 07265328 | 10/1995 |
| JP | 8-317936 | 3/1996 |
| JP | 08056955 | 3/1996 |
| JP | 8-289895 | 5/1996 |
| JP | 08252263 | 10/1996 |
| JP | 8-317934 | 12/1996 |
| JP | 9-000538 | 1/1997 |
| JP | 09010223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |
| WO | WO 2008045348 | 4/2008 |
| WO | WO 2009039179 | 3/2009 |

OTHER PUBLICATIONS

Japanese Office Action dated May 7, 2015, issued in Japanese Application No. 2011-122555.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/860,324, filed Apr. 10, 2013, Kappus.
U.S. Appl. No. 13/868,732, filed Apr. 23, 2013, Mueller.
U.S. Appl. No. 13/873,780, filed Apr. 30, 2013, Kerr.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.

(56) References Cited

OTHER PUBLICATIONS

U.S. Appl. No. 13/969,278, filed Aug. 16, 2013, Kerr.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.

(56) References Cited

OTHER PUBLICATIONS

Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1. 2007.
Int'l Search Report EP 06020756.0. dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/USO4/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US05/52460 dated Apr. 24, 2008.
Int'l Search Report PCT/US08/61498 dated Sep. 22, 2008.
Int'l Search Report PCT/US09/032690 dated Jun. 16, 2009.
International Search Report EP11168419.7 dated Aug. 8, 2011.
International Search Report EP11168419.7 dated Oct. 11, 2011.
European Search Report for European Application No. 11168458 dated Jul. 29, 2011.
European Search Report for European Application No. 12169753.6 dated Sep. 14, 2012.
European Search Report for European Application No. 11168458.5 dated Jul. 21, 2011.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.

* cited by examiner

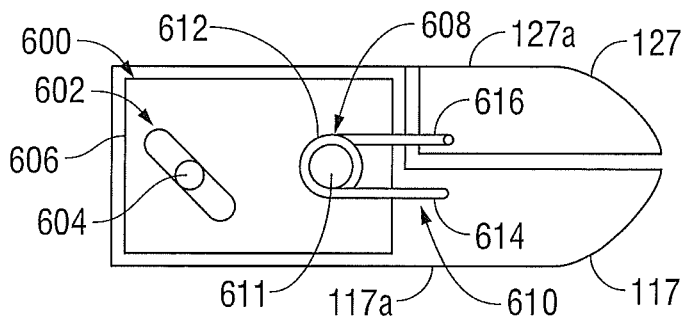
FIG. 5
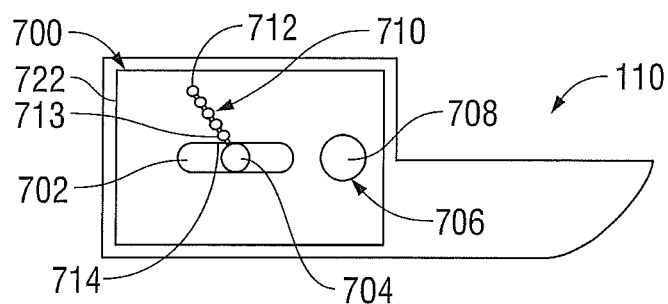
FIG. 6
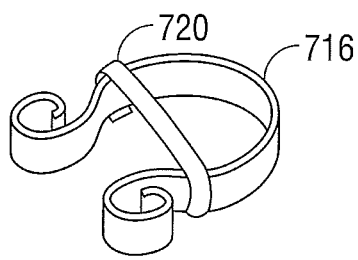 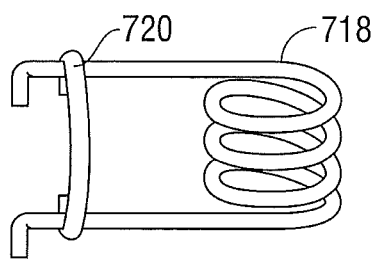
FIG. 7A  FIG. 7B

APPARATUS FOR PERFORMING AN ELECTROSURGICAL PROCEDURE

CROSS-REFERENCE TO RELATED APPLICATIONS

This application is a continuation of U.S. patent application No. 12/792,001 (now U.S. Pat. No. 8,491,624), filed Jun. 2, 2010, the contents of which is hereby incorporated by reference in its entirety.

BACKGROUND

1. Technical Field

The present disclosure relates to an apparatus for performing an electrosurgical procedure. More particularly, the present disclosure relates to an electrosurgical apparatus including an end effector assembly having a pair of jaw members with a jaw insert providing a mechanical advantage at the end effector while maintaining an electrical insulative barrier between seal plates associated with the jaw members and one or more of operative components associated with the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical instrument is operatively and selectively coupled to an RF power source (e.g., RF generator) that is in operative communication with a control system for performing an electrosurgical procedure. Electrosurgical forceps utilize both mechanical clamping action and electrical energy to effect hemostasis by heating the tissue and blood vessels to coagulate, cauterize, seal, cut, desiccate, and/or fulgurate tissue.

Typically, the jaw members include a respective highly conductive seal plate and are pivotably coupled to one another via one or more mechanical interfaces that provide a point of pivot for one or both of the jaw members. For example, in certain instances, a cam slot including a cam pin operably disposed therein and a pivot pin may be operably coupled to the end effector and/or one or both of the jaw members. In this instance, the cam slot, cam pin and pivot pin collectively pivot and close one or both of the jaw members. For added structural integrity, the cam slot, cam pin and pivot pin may be fabricated from metal. However, because the metal typically utilized in fabricating the cam slot, cam pin and pivot pin is highly conductive, the cam slot, cam pin and pivot pin need to be electrically insulated from the seal plates associated with the respective jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, a spring is typically operatively associated with a drive assembly to facilitate actuation of a movable handle associated with the handle assembly to ensure that a specific closure force between the jaw members is maintained within one or more suitable working ranges.

An increased mechanical advantage and/or mechanical efficiency with respect to transferring the closure force(s) from the handle assembly to the jaw members while maintaining an electrical insulative barrier between the seal plates associated with the jaw members may prove advantageous in the relevant art.

SUMMARY

The present disclosure provides a forceps. The forceps includes a housing having one or more shafts that extend therefrom that define a longitudinal axis therethrough. An end effector assembly operatively connects to a distal end of the shaft(s) and has a pair of first and second jaw members. The first and second jaw members movable relative to one another from an open position wherein the first and second jaw members are disposed in spaced relation relative to one another, to a clamping position wherein the first and second jaw members cooperate to grasp tissue therebetween. A jaw insert is operably disposed within one or both of the first and second jaw members. The jaw insert includes one or more cam slots defined therein configured to receive a cam pin that upon movement thereof rotates the first and second jaw members from the open position to the clamping position and an opening defined therein configured to house a pivot pin that provides a point of pivot for the first and second jaw members. The jaw insert may be manufactured from an insulative medium to dielectrically isolate the first and second jaw members.

In an embodiment, the forceps includes a housing having one or more shafts that extend therefrom that define a longitudinal axis therethrough. An end effector assembly operatively connects to a distal end of the shaft(s) and has a pair of first and second jaw members. The first and second jaw members movable relative to one another from an open position wherein the first and second jaw members are disposed in spaced relation relative to one another, to a clamping position wherein the first and second jaw members cooperate to grasp tissue therebetween. A jaw insert is operably disposed within one or both of the first and second jaw members. The jaw insert includes one or more cam slots defined therein configured to receive a cam pin that upon movement thereof rotates the first and second jaw members from the open position to the clamping position and an opening defined therein configured to securely house a pivot pin that provides a point of pivot for the first and second jaw members. A spring operably couples to the jaw insert and is configured to provide a camming force to the cam slot and a portion of a sealing force to the jaw members when the first and second jaw members are in a clamping position.

In one particular embodiment, a spring operably couples to the jaw insert, and provides a camming force to the cam slot and a sealing force to the jaw members when the first and second jaw members are in a clamping position.

In one particular embodiment, the jaw insert is manufactured from an insulative medium to dielectrically isolate the first and second jaw members and a spring operably couples to the jaw insert. The spring is configured to provide a camming force to the cam slot and a portion of a sealing force to the first and second jaw members when the first and second jaw members are in a clamping position.

The present disclosure also provides a method of manufacture for an electrosurgical instrument. The method includes an initial step of fabricating a housing including a handle assembly and one or more shafts wherein the shaft(s) defines a longitudinal axis. A step of the method includes fabricating an end effector, wherein the end effector is operably positionable at a distal end of the shaft(s). The end effector includes a pair of first and second jaw members. One or both of the first and second jaw members includes an opening. Fabricating a jaw insert including one or more cam slots defined therein configured to receive a cam pin that upon movement thereof rotates the first and second jaw members from an open position to the clamping position and an opening defined therein configured to securely house a pivot pin that provides a point of pivot for the first and second jaw members is a step of the method. Positioning the insulative jaw insert within the opening of one of the first and second jaw members is another step of the method.

BRIEF DESCRIPTION OF THE DRAWING

Various embodiments of the present disclosure are described hereinbelow with references to the drawings, wherein:

FIG. 3A-1 is a cross-section view taken along line segment 3A-1 of FIG. 3A;

FIG. 5 is a schematic view of a jaw member including a jaw insert according to yet another embodiment of the present disclosure;

FIG. 6 is a schematic view of a jaw member including a jaw insert according to still another embodiment of the present disclosure;

FIG. 7A is a perspective view of a spring configuration that may be utilized with the jaw insert depicted in FIGS. 2A-5 or FIG. 6;

FIG. 7B is a perspective view of another type of spring configuration that may be utilized with the jaw insert depicted in FIGS. 2A-5 or FIG. 6;

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
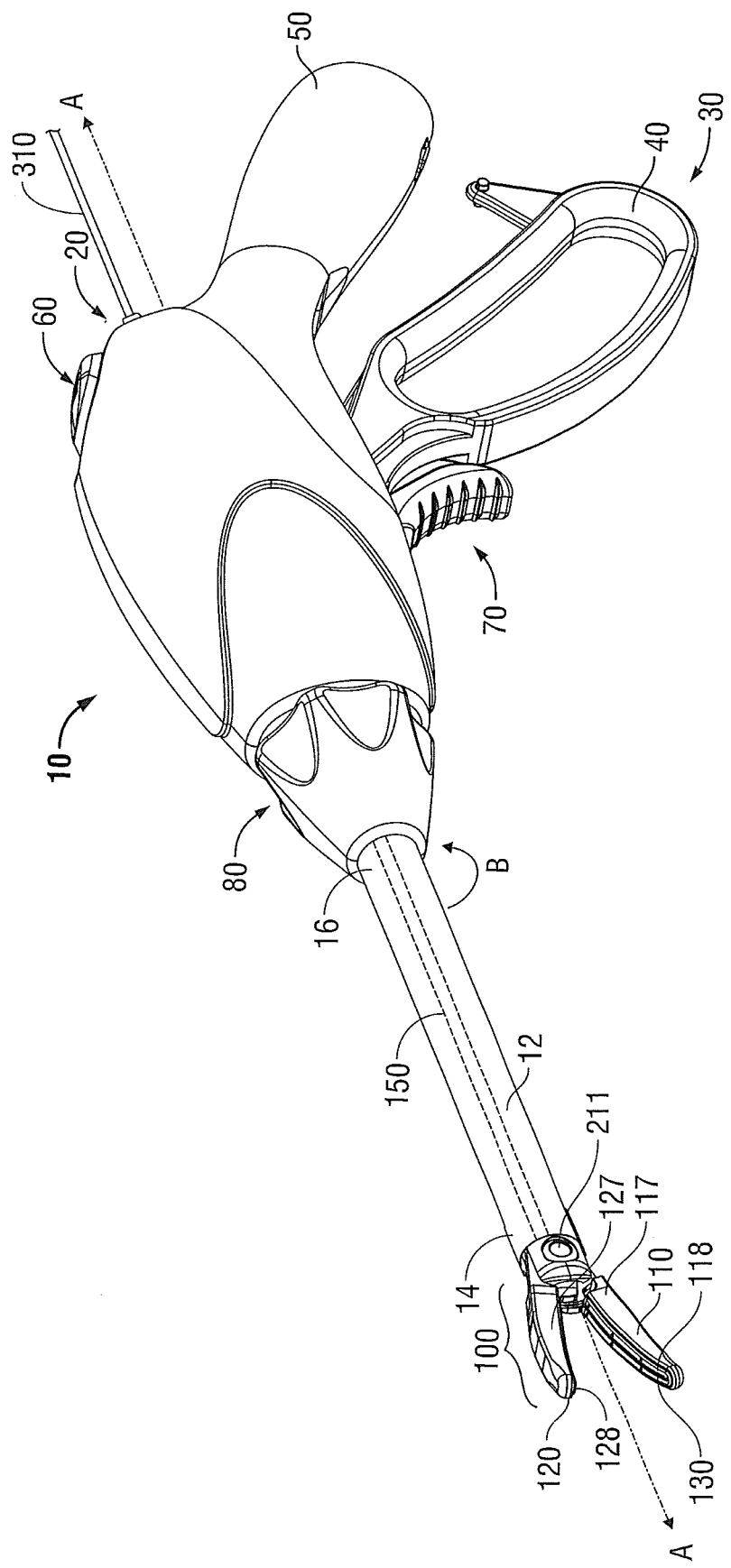
FIG. 1A is a side, perspective view of an endoscopic bipolar forceps showing an end effector assembly including jaw members according to an embodiment of the present disclosure.
Figure 1B:
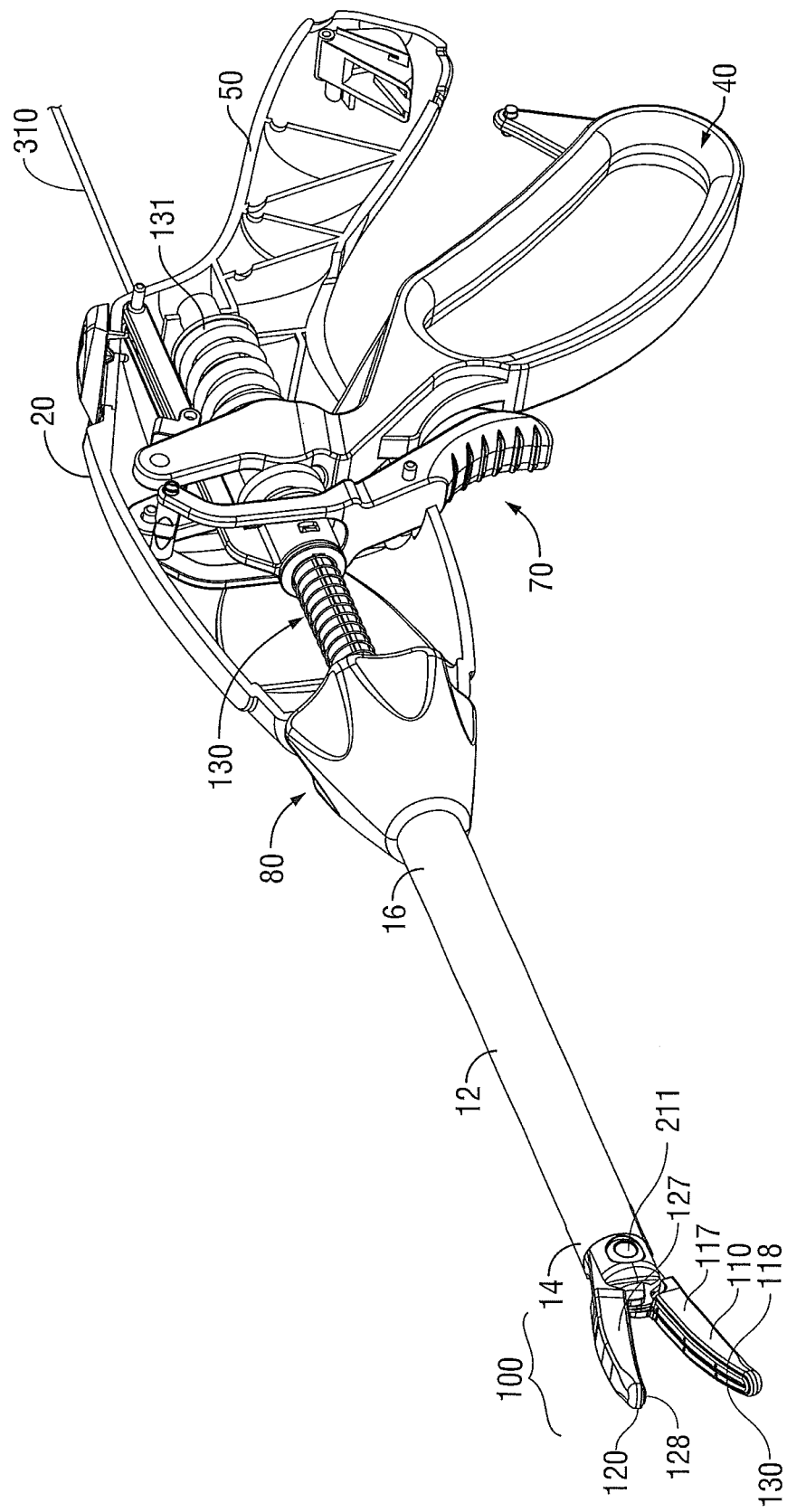
FIG. 1B is a side, perspective view of the endoscopic bipolar forceps depicted in FIG. 1A illustrating internal components associated with a handle assembly associated with the endoscopic bipolar forceps.

With reference to FIGS. 1A and 1B, an illustrative embodiment of an electrosurgical apparatus (e.g., bipolar forceps 10) for performing an electrosurgical procedure is shown. Bipolar forceps 10 is operatively and selectively coupled to an electrosurgical generator (not shown) for performing an electrosurgical procedure. As noted above, an electrosurgical procedure may include sealing, cutting, cauterizing coagulating, desiccating, and fulgurating tissue all of which may employ RF energy. The generator may be configured for monopolar and/or bipolar modes of operation. The generator may include or is in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., a cable 310) to one or both seal plates 118, 128.

Bipolar forceps 10 is shown for use with various electrosurgical procedures and generally includes a housing 20, an electrosurgical cable 310 that connects the forceps 10 to a source of electrosurgical energy (e.g., electrosurgical generator not shown), a handle assembly 30, a rotating assembly 80, a trigger assembly 70, a drive assembly 130 (FIG. 1B), and an end effector assembly 100 that operatively connects to the drive assembly 130 that includes a drive rod 150. The drive assembly 130 may be in operative communication with handle assembly 30 for imparting movement of one or both of a pair of jaw members 110, 120 of end effector assembly 100. End effector assembly 100 includes opposing jaw members 110 and 120 (FIGS. 1A and 1B) that mutually cooperate to grasp, seal and, in some cases, divide large tubular vessels and large vascular tissues.

With continued reference to FIGS. 1A and 1B, forceps 10 includes a shaft 12 that has a distal end 14 configured to mechanically engage the end effector assembly 100 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is ultimately connected to the drive assembly 130, which together mechanically cooperate to impart movement of one or both of the jaw members 110 and 120 to move from an open position, wherein the jaw members 110 and 120 are disposed in spaced relation relative to one another, to a clamping or closed position, wherein the jaw members 110 and 120 cooperate to grasp tissue therebetween.

Jaw members 110, 120 are operatively and pivotably coupled to each other and located adjacent the distal end 14 of shaft 12. A respective electrically conductive seal plate 118 and 128 is operably supported on and secured to jaw housings 117 and 127 of respective the jaw members 110 and 120, described in greater detail below. For the purposes herein, jaw members 110 and 120 include jaw housings 117 and 127 and sealing plates 118 and 128, respectively. Jaw housings 117 and 128 are configured to support the seal plates 118 and 128, respectively.

For a more detailed description of the bipolar forceps 10 including handle assembly 30 including movable handle 40, rotating assembly 80, trigger assembly 70, drive assembly 130, jaw members 110 and 120 (including coupling methods utilized to pivotably couple the jaw members 110 and 120 to each other) and electrosurgical cable 310 (including line-feed configurations and/or connections), reference is made to commonly owned U.S. patent application Ser. No. 11/595,194 filed on Nov. 9, 2006.

Figure 2A:
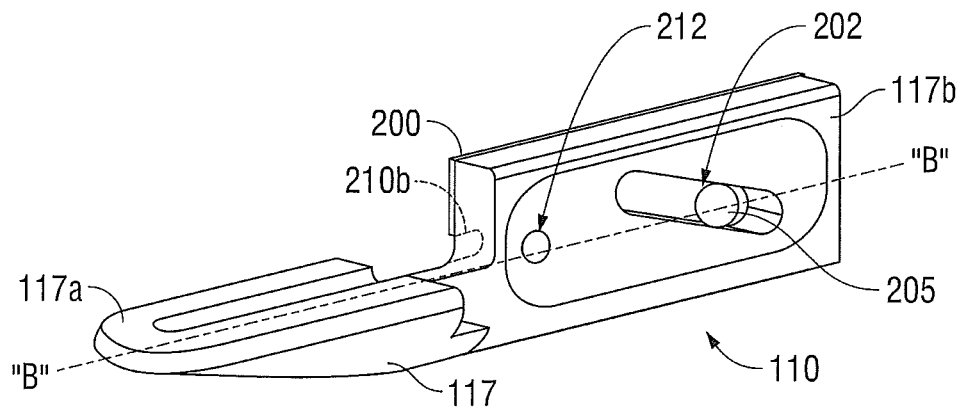
FIG. 2A is a perspective view of a jaw member illustrated in FIGS. 1A and 1B including a jaw insert according to an embodiment of the present disclosure.
Figure 2B:
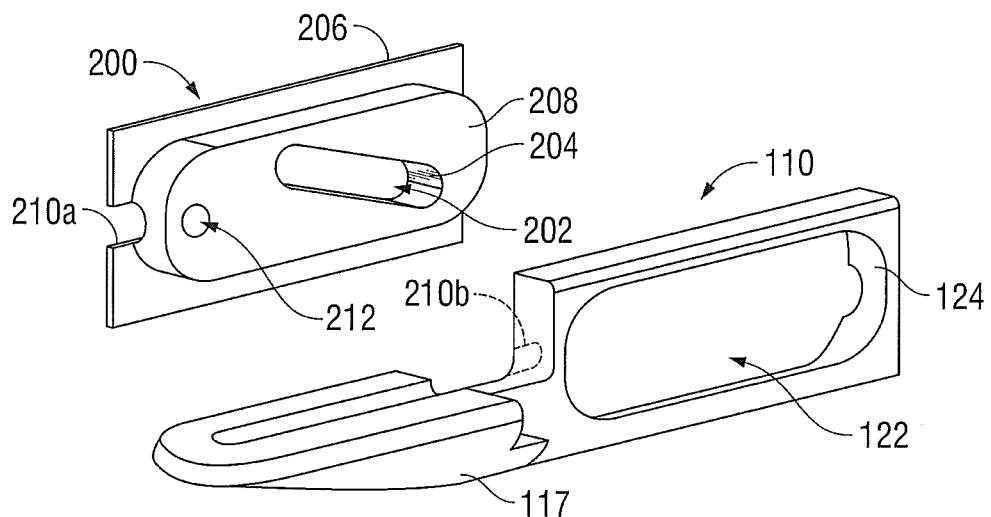
FIG. 2B is an exploded view of the jaw member and jaw insert illustrated in FIG. 2A.

Turning now to FIGS. 2A-2B, and initially with reference to FIG. 2A, jaw housing 117 is shown operably coupled to a jaw insert 200 according to an embodiment of the present disclosure. It should be noted that jaw insert 200 may be operably coupled to either or both of the jaw housings 117 and 127. In view thereof, and so as not to obscure the present disclosure with redundant information, the operative components associated with the jaw insert 200 are described in further detail with respect to jaw member 110, and only those features distinct to housing 127 will be described hereinafter.

Jaw member 110 and operative components associated therewith may be formed from any suitable material, including but not limited to metal, metal alloys, plastic, plastic composites, and so forth. In the embodiment illustrated in FIGS. 2A and 2B, jaw member 110 is formed from metal.

A distal end 117a of the jaw member 110 may be configured to securely engage the electrically conductive seal plate 118 or, with respect to a monolithic jaw member, form the seal plate 118. As discussed herein, jaw member 110 is monolithic but one such assembled jaw member is disclosed in commonly-owned U.S. patent application Ser. No. 11/827,297.

A proximal end 117b of the jaw member 110 is configured to securely support a portion of the jaw insert 200 in a relatively fixed position. With this purpose in mind, proximal end 117b has a generally rectangular configuration including a recess or opening 122 defined therein that includes geometry of suitable proportion to securely house the jaw insert 200 (FIG. 2B). In the embodiment illustrated in FIGS. 2A-2B, opening 122 of proximal end 117b includes a generally oval or elliptical configuration defined by a generally oval sidewall 124 having four generally arcuate corners (FIG. 2B). More particularly, opening 122 and/or sidewall 124 includes a generally oval configuration having a height, length and width each proportioned to securely house jaw insert 200 within the jaw member 110 during the manufacture process of the jaw member 110, end effector 100 and/or forceps 10. A portion of the proximal end 117b is operably secured to the distal end 14 of the shaft 12. More particularly, a portion of proximal end 117b operably couples to the distal end 14 and is in operative communication with the drive rod 150 of the drive assembly 130 such that movement of the drive rod 150 causes one or both of the jaw members 110 and 120 to move from the opened position to the closed or clamping position. For example, in one particular embodiment, when the drive rod 150 is "pulled," i.e., moved or translated proximally, one or both of the jaw members 110 and 120 is/are caused to move toward the other. In an alternate embodiment, when the drive rod 150 is "pushed," i.e., moved or translated proximally, one or both of the jaw members 110 and 120 are caused to move toward each other. In certain instances, it may prove useful to have a drive rod 150 that is flexible. More particularly, in the instance where the drive rod 150 is operatively associated with a catheter instrument (e.g., a catheter forceps configured for use in catheter based applications where the jaws associated therewith are typically quite small, i.e., 3 mm-5 mm), the drive rod 150 may be flexible to accommodate bends typically associated with a shaft of the catheter forceps when the catheter forceps is positioned within a patient and when the jaws are being moved from an open configuration for positioning tissue between the jaws, to a closed configuration for grasping tissue.

Jaw insert 200 defines a cam slot 202 and a pivot pin opening 212 each configured such that one or both of the jaw members, e.g., jaw member 110, may pivot with respect to the other jaw member, e.g., jaw member 120, while providing electrical insulation for the cam slot 202 and a pivot pin 211 (see FIG. 1A, for example) from one or more electrical components associate with one or both of the jaw members 110 and 120. To this end, jaw insert 200 may be made from a non-conductive (or partially conductive) material. Suitable materials that jaw insert 200 may be formed from include but are not limited to plastic, ceramic, and so forth. For example, jaw insert 200 may be made from injected molded plastic, such as, for example, a plastic of the type selected from the group consisting of thermoplastics and thermoset plastics. In the embodiment illustrated in FIGS. 2A and 2B, jaw insert 200 is made a thermoset type plastic. In one particular embodiment, jaw insert 200 is made from a thermosetting plastic, such as, for example, Duroplast.

Jaw insert 200 includes a generally rectangular base 206 including a generally oval or elliptical raised portion 208 of suitable proportion and configured to securely engage sidewall 124 of the opening 122 (see FIG. 2A in combination with FIG. 2B). A generally circular cut-out 210a is positioned at a distal end of the jaw insert 200 and is configured to securely engage a corresponding detent or protrusion 210b (shown in phantom, see FIGS. 2A and 2B) operably disposed on the jaw member 110. This cut-out 210a and detent 210b configuration facilitates maintaining the jaw insert 200 and jaw member 110 in alignment and secured engagement with each other.

Jaw insert 200 may be secured to jaw member 110 via any suitable securement methods known in the art. For example, securement of jaw insert 200 to jaw member 110 may be accomplished by stamping, by overmolding, by overmolding a stamped non-conductive jaw insert 200 and/or by overmolding a plastic injection molded jaw insert 200. All of these manufacturing techniques produce a jaw member, e.g., jaw member 110, having a jaw insert 200 that is substantially surrounded by the jaw housing 117. Alternatively, jaw insert 200 may be secured to jaw member 110 via one or more types of mechanical interfaces. More particularly, jaw insert 200 may be secured to jaw member 110 via a press fit, fiction fit, bayonet fit, etc. In one particular embodiment, jaw insert 200 is secured to jaw member 110 via press fit. In this instance, one or more grooves or indents (not explicitly shown) may be operably disposed along generally oval sidewall 124. The groove(s) is configured to securely and operably engage a corresponding detent(s) (not explicitly shown) operably disposed on the jaw insert 200. For example, the corresponding detent(s) may be operably disposed along an outer periphery of the generally oval raised portion 208. The groove(s) and detent(s) maintain the jaw insert 200 and jaw member 110 in secured engagement when the jaw insert 200 is positioned within the jaw member 110.

Cam slot 202 is of suitable proportion and configured to receive a corresponding camming structure 205, e.g., a cam pin 205, see FIG. 2A, and is operably formed and/or positioned on the jaw insert 200. More particularly, cam slot 200 includes a generally oblique configuration with respect to a longitudinal axis "B-B" that is parallel to longitudinal axis "A-A" defined through the shaft 12, see FIG. 2A. Cam slot 202 may extend at an angle that ranges from about 5° to about 45° with respect to the longitudinal axis "B-B." In the embodiment illustrated FIGS. 2A and 2B, cam slot 202 extends at angle that is approximately equal to 30° with respect to the longitudinal axis "B-B." Cam slot 202 extends through the jaw insert 200, see FIGS. 2A and 2B. One or more type of lubricious materials 204 (illustrated via hatching in FIG. 2B), e.g., PTFE, may coat cam slot 202. Coating the cam slot 202 with the lubricious material 204 facilitates movement of the cam pin 205 within the cam slot 202 when the drive rod is translated distally (or proximally). The angle of the cam slot 202 may be selectively varied depending upon a particular instrument, use or manufacturing preference. As such, an assembly technician can insert a variety of different jaw inserts 200 to accomplish a particular purpose.

An aperture or opening 212 of suitable proportion and configured to receive a corresponding pivot pin 211 or the like (see FIG. 1A) is operably formed and/or positioned on the jaw insert 200. More particularly, aperture 212 includes a generally circumferential configuration and is operably disposed at a distal end of the jaw insert 200. Aperture 212 extends through the jaw insert 200, see FIGS. 2A and 2B. Aperture 212 may be oriented in any other position within the jaw insert 200 depending upon a particular purpose or a particular instrument.

In an assembled configuration each of the jaw members 110 and 120 are positioned in side-by-side relation. Cam pin 205 is operably disposed within cam slot 202 associated with jaw member 110 and a corresponding cam slot (not explicitly shown) associated with jaw member 120. As noted above, the cam pin 205 may be operably coupled to the drive rod 150 (or other suitable driving device). A pivot pin 211 is positioned within opening 212 associated with jaw member 110 and a corresponding opening (not explicitly shown) associated with jaw member 120. The pivot pin 211 provides a point of pivot for each of the jaw members 110 and 120. Once assembled, the jaw members 110 and 120 may be pivotably supported at the distal end 14 of the shaft 12 by known methods, such as, for example, by the method described in commonly-owned U.S. patent application Ser. No. 11/827, 297.

In use, initially jaw members 110 and 120 are in an opened position. Tissue is positioned between the jaw members 110 and 120 and, subsequently, movable handle 40 is moved proximally. Proximal movement of movable handle 40 causes the drive rod 150 to move proximally. Proximal movement of drive rod 150 causes cam pin 205 positioned within the cam slot 202 and the cam slot associated with jaw member 120 to move proximally, which, in turn, causes one or both of the jaw members, e.g., jaw member 110 to move (e.g., pivot about the pivot pin 211 positioned in opening 212 and the opening associated with jaw member 120) toward the other jaw member, e.g., jaw member 120, such that tissue is clamped between the jaw members 110 and 120. Thereafter, electrosurgical energy is transmitted to the seal plates 118 and 128 of respective jaw members 110 and 120 such that a desired tissue effect is caused to the clamped tissue. During transmission of electrosurgical energy to the seal plates 118 and 128, jaw insert 200 serves as an electrical insulation medium or barrier between the seal plates 118, 128 and the cam pin 211 positioned within the cam slot 202 (and the cam slot associated with jaw member 120), and pivot pin 211 positioned within the opening 212 (and the opening associated with jaw member 120). This configuration also prevents and/or impedes electrical shorts from developing between the seal plates 118, 128 and jaw housings 117 and 127, and the cam pin 211 positioned within the cam slot 202 (and the cam slot associated with jaw member 120), and pivot pin 211 positioned within the opening 212 (and the opening associated with jaw member 120). Preventing and/or impeding electrical shorts from developing between one or more of the operative components associated with the end effector 100 provides improved transmission of electrosurgical energy from an electrosurgical power source to the seal plates 118 and 128.

Figure 3A:
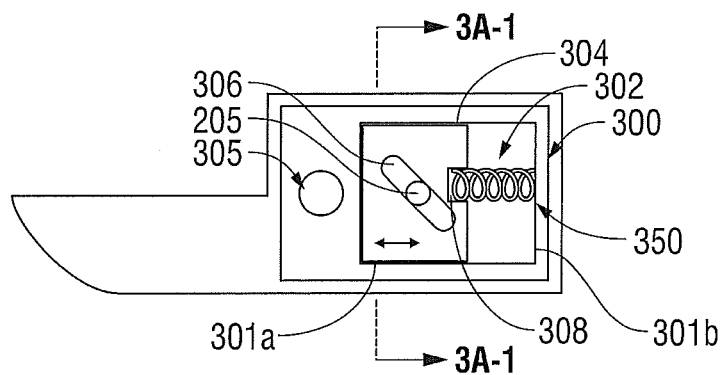
FIG. 3A is a schematic view of a jaw member including a jaw insert according to another embodiment of the present disclosure.
Figures 1, 3A:
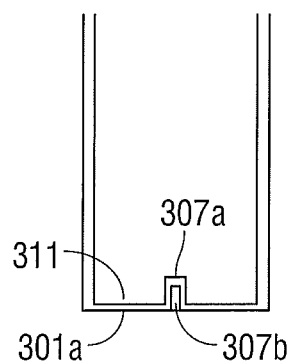
Figure 3B:
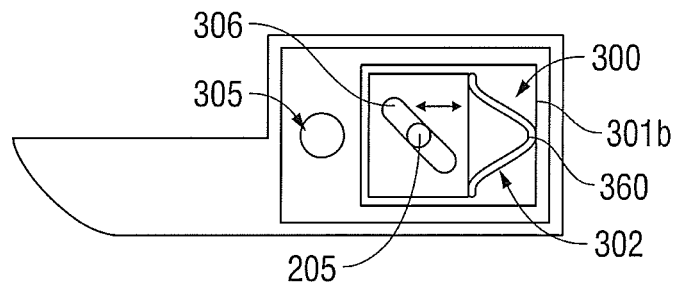
FIG. 3B is a schematic view of a jaw member including a jaw insert according to an alternate embodiment of the jaw insert illustrated in FIG. 3A.
Figure 3C:
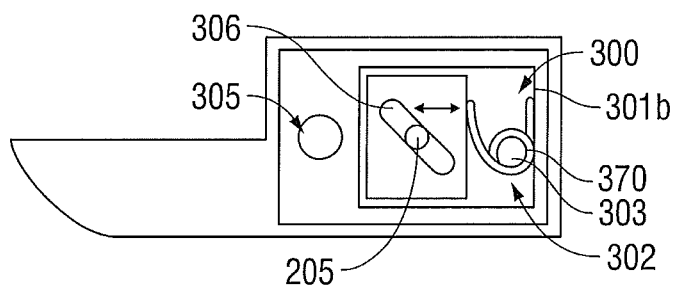
FIG. 3C is a schematic view of a jaw member including a jaw insert according to an alternate embodiment of the jaw insert illustrated in FIG. 3A.

With reference now to FIGS. 3A-3C an alternate embodiment of a jaw insert 300 is shown. Jaw insert 300 is similar to jaw insert 200 and so as not to obscure the present disclosure with redundant information, only those operative features and components that are unique to jaw insert 300 are described. In the embodiment illustrated in FIG. 3A, jaw insert 300 is described in terms of use with the jaw member 110. In the embodiment illustrated in FIG. 3A, jaw member 110 and operative components associated therewith function in a manner as described above with respect to jaw insert 200. Accordingly, only those features and operative components associated with jaw member 110 that are necessary to facilitate understanding of the operative components associated with jaw insert 300 is described.

An opening 302 associated with the jaw insert 300 and defined therein is configured to house one or more resilient members 350 and a movable member 304 that includes a cam slot 306 and an opening 305 (similar to that of opening 212 of jaw insert 200). More particularly, opening 302 is dimensioned such the resilient member(s) 350 is capable of flexing and movable member 304 is capable of translating or moving within the opening 302. To this end, opening 302 is defined by four walls of the jaw insert 300 forming a generally square or rectangular configuration. In an embodiment, one or more of the walls, e.g., a bottom wall 301a, may include a groove or detent that slidable engages a corresponding detent or groove operably disposed on the movable member 304, e.g., a bottom surface 311 of the movable member 304. For example, a longitudinal detent 307b may extend along a length of the bottom wall 301a of the opening 302 and a corresponding longitudinal groove 307a of suitable proportion may extend along a length of the bottom surface 311 of the movable member 304, see FIG. 3A-1. In this instance, the groove 307a and detent 307b configuration facilitates movement of the movable member 304 with respect to the jaw insert 300 and maintains the movable member 304 in substantial alignment with the longitudinal axis "A-A," see FIG. 3A in combination with 3A-1. A proximal wall 301b of the opening 302 is operably coupled to the resilient member 350 via one or more suitable coupling methods, e.g., adhesive, solder, etc. A portion of the movable member 304 operably couples to the resilient member 350.

Movable member 304 is suitably proportioned to movably reside within the opening 302. Cam slot 306 is operably disposed within the movable portion 304 and is similar to cam slot 204. One distinguishing feature of cam slot 306 when compared to cam slot 202 is the position of cam slot 306 with respect to jaw insert 300. That is, cam slot 304 is positioned closer to a distal end of the jaw insert 300 than cam slot 202 is positioned with respect to a distal end of the jaw insert 200.

Positioning the cam slot 304 closer to the distal end of the jaw insert 300 provides more area for the resilient member 350 to expand and contract when the jaw members 110 and 120 are moved from an opened to closed or clamping position or vice versa. In one particular embodiment, a notched area 308 disposed adjacent a proximal end of the movable member 304 is dimensioned to securely house a portion of resilient member 350. In an alternate embodiment, a proximal end of the movable member 304 is configured to securely house a portion of resilient member 350.

One or more types of resilient member(s) 350 are operably associated with the jaw insert 300. More particularly, one or more types of springs are utilized to generate a closure force at the jaw members 110 and 120 of the end effector 100 when the jaw members 110 and 120 are in a closed or clamped position. The resilient member 350 cooperates with the drive assembly 130 to provide the necessary closure force for sealing tissue. More particularly, the resilient member 350 offloads some of the forces necessary to generate the appropriate closure force which is typically incurred in the housing 20. A compression spring 131 (see FIG. 1B) in housing 20 and the resilient member 350 are configured to mechanically assist a user when moving the handle 40 to generate the necessary drive forces.

One or more suitable types of springs may be utilized to generate a sealing force at cam slot 304 of the movable member 304. In the embodiment illustrated in FIG. 3A, a coil spring 350 is operably associated with the jaw insert 300. More particularly, a proximal end of the coil spring 350 is operably coupled to the proximal wall 301b of the jaw insert 300 and a distal end of the spring 350 is securely housed within the notched area 308. The coil spring 350 may have any suitable rating, e.g., in one particular embodiment, spring 350 has a rating of about 120 pounds per square inch to offset all of the closure forces from the handle assembly 30 and the drive assembly 130. Lesser spring ratings are envisioned when the coil spring 350 or other type of spring is manufactured to assist with sealing pressures.

In an alternate embodiment, spring 350 may be a leaf spring 360, see FIG. 3B, for example. In the embodiment illustrated in FIG. 3B, proximal end of the leaf spring 360 couples to the proximal wall 301b of the jaw insert 300 and a pair of distal ends of the leaf spring 360 couples to a proximal end of the movable member 304. Each of the proximal and distal ends of the leaf spring 360 couples to a respective proximal wall 301b of the jaw insert and proximal end of the movable member 304 by methods previously described above.

In an alternate embodiment, spring 350 may be a torsion spring 370, see FIG. 3C, for example. In the embodiment illustrated in FIG. 3C, proximal end of the torsion spring 306 couples to the proximal wall 301b of the jaw insert 300 and a distal end of the torsion spring 370 couples to a proximal end of the movable member 304. The proximal end of the torsion spring 370 couples to the proximal wall 301b of the jaw insert 300 via a pin 303 (or other suitable structure or other suitable methods, e.g., such as the methods previously described above with respect to spring 350). The distal end of the spring 370 couples to the proximal end of the movable member 304 by methods previously described above with respect to spring 350.

Operation of the forceps 10 with an jaw insert 300 that includes a resilient member 350 is described below in terms of use with a coil spring 350 illustrated in FIG. 3A.

In use, initially jaw members 110 and 120 are in an opened position. Tissue is positioned between the jaw members 110 and 120 and, subsequently, movable handle 40 is moved proximally. Proximal movement of movable handle 40 causes the drive rod 150 to move proximally. Proximal movement of the drive rod 150 causes a cam pin, e.g., cam pin 205, positioned within the cam slot 306 on movable member 304 to move proximally against the bias of the coil spring 350, which, in turn, causes one or both of the jaw members, e.g., jaw member 110 to move toward the other jaw member, e.g., jaw member 120, such that tissue is clamped between the jaw members 110 and 120. When the cam pin 205 is moved, i.e., "pulled," to a set position, e.g., a position when the jaw members 110 and 120 are in the closed or clamped position, the biased cam pin 205 generates a sealing or closure force at the jaw members 110 and 120. Thereafter, the previously described steps with respect to jaw insert 200 may be carried out. The combination of jaw insert 300 with a coil spring 350 assists in providing a consistent, uniform tissue effect, e.g., tissue seal, and an electrical insulation barrier between the seal plates 118, 128 and one or more of the operative components described above with respect to jaw insert 200. The combination of jaw insert 300 and coil spring 350 (or other described springs, e.g., leaf spring 360) may provide an additional mechanical advantage when employed with surgical devices with small jaws, such as, for example, flexible catheters that employ small jaws configured for jaw insertion into surgical ports of relatively small dimension. Additionally, the coil spring 350 (or other biasing member) may be configured to generate all of the closure force necessary to seal tissue.

Figure 3D:
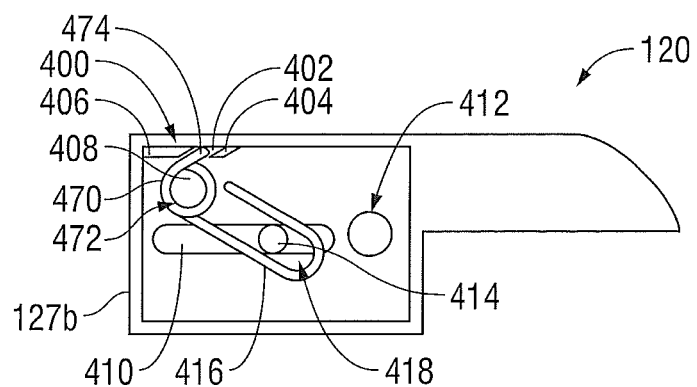
FIG. 3D is a schematic view of a jaw member including a jaw insert according to an alternate embodiment of the jaw insert illustrated in FIG. 3A.

With reference now to FIG. 3D an alternate embodiment of a jaw insert 400 is shown. Jaw insert 400 is similar to jaw inserts 200 and 300. So as not to obscure the present disclosure with redundant information, only those operative features and components that are unique to jaw insert 400 are described. For illustrative purposes, jaw insert 400 and operative components associated therewith are described in terms of use with jaw member 120.

A proximal portion of the jaw insert 400 includes a notched area or channel 402 defined by two raised portions 404 and 406. The notched area 402 is proportioned and configured to securely house a portion of a proximal end of a torsion spring 470, described in greater detail below. A raised protrusion or pin 408 of suitable proportion is configured to securely engage an opening at the proximal end of the torsion spring 470. A cam slot 410 similar to previously described cam slots, e.g., cam slot 306, is operably disposed on the jaw insert 400. Cam slot 410 houses a cam pin 414 that is movable within cam slot 410 from a proximal position to a distal position or vice versa. A distinguishing feature of the cam slot 410 when compared to previously described cam slots, e.g., cam slot 306, is that cam slot 410 is orientated in a direction that is substantially parallel, i.e., horizontal, to the longitudinal axis "A-A." Cam slot 410 is in substantial alignment with an opening 412 that houses a pivot pin, e.g., pivot pin 211. Opening 412 is configured in a manner similar to previously described openings, e.g., 212.

In the embodiment illustrated in FIG. 3D, torsion spring 470 is operably associated with the jaw insert 400. More particularly, an opening 472 (shown engaged with protrusion 408 and as such not explicitly visible) is defined at the proximal end of the torsion spring 470 and is securely engaged to protrusion 408. An elongated portion 416 defining a slot 418 extends from opening 472 of the torsion spring 470 and engages cam pin 414 of cam slot 410. A proximal end of the torsion spring 470 is securely housed within the notched area 402 of the jaw insert 400. More particularly, a finger 474 of suitable proportion extends from the proximal end of the torsion spring 470 and is securely housed within the notched area 402.

Operation of the forceps 10 with jaw insert 400 that includes a torsion spring 470 is substantially similar to the operation of a forceps 10 that includes a spring depicted in FIGS. 3A-3C. One distinguishing feature of the jaw insert 400 when compared to jaw insert 300 utilized is that jaw member 120 pivots with respect to the jaw member 110.

Figure 4A:
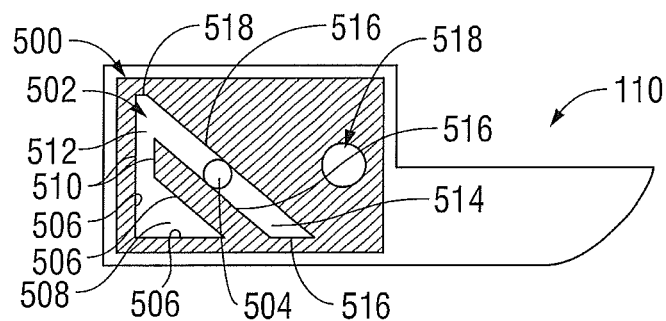
FIG. 4A is a schematic view of a jaw member including a jaw insert according to still another embodiment of the present disclosure.
Figure 4B:
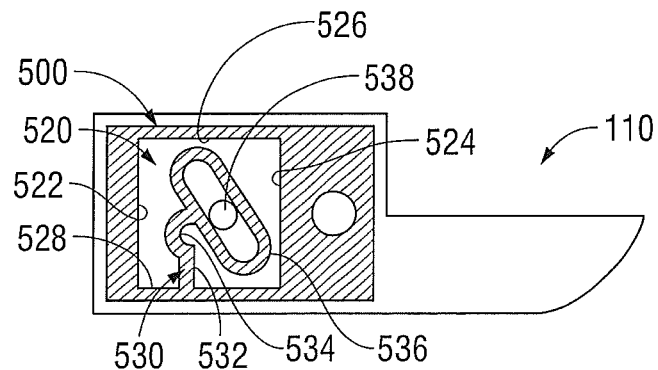
FIG. 4B is a schematic view of a jaw member including a jaw insert according to an alternate embodiment of the jaw insert illustrated in FIG. 4A.
Figure 4C:
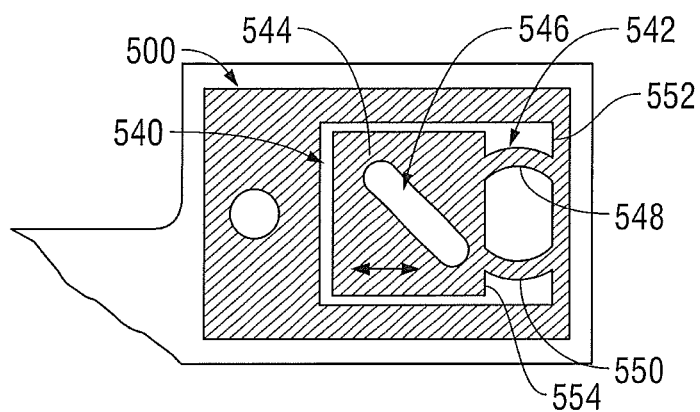
FIG. 4C is a schematic view of a jaw member including a jaw insert according to an alternate embodiment of the jaw insert illustrated in FIG. 4A.

With reference now to FIGS. 4A-4C, and initially with reference to FIG. 4A, an alternate embodiment of jaw inserts 200, 300 and 400 is shown and designated 500. Jaw insert 500 is similar to jaw inserts 200, 300 and 400. So as not to obscure the present disclosure with redundant information, only those operative features and components that are unique to jaw insert 500 are described. For illustrative purposes, jaw insert 500 and operative components associated therewith are described in terms of use with jaw member 110. In the embodiments illustrated in FIG. 4A-4C, jaw member 110 and operative components associated therewith function in a manner as described above with respect to the previously described jaw inserts, e.g., jaw insert 200. Accordingly, only those features and operative components associated with jaw member 110 that are necessary to facilitate understanding of the operative components associated with jaw insert 500 are described.

In the embodiments illustrated in FIGS. 4A-4C, one or more types of resilient or spring-like structures are monolithically formed with the jaw insert 500 during the manufacturing process. Monolithically forming the jaw insert 500 with a resilient member(s) decreases the amount of working components, e.g., coil spring 350, needed to provide the closure or sealing forces at the jaw members 110 and 120, which, in turn, reduces the overall cost in the manufacture of the end effector 100 and/or jaw members 110 and 120.

With reference to FIG. 4A, jaw insert 500 includes a monolithically formed notched area 502 having suitable dimensions. Notched area 502 creates a cantilever spring configuration. More particularly, the cantilever spring configuration is defined by a notched area 502 that includes three sidewalls 506 that collectively define a generally triangular base section 508 of suitable dimensions. A pair of sidewalls 510 extends from the base section 508 and defines an upright section 512 of suitable dimensions. The upright section 512 is oriented orthogonal with respect to the longitudinal axis "A-A." A spring arm section 514 is defined by three sidewalls 516 extending distally from the upright section 512 in a generally oblique manner toward an opening 518 that is configured to house a pivot pin, e.g., pivot pin 211 (not shown in this FIG.). Opening 512 is configured and functions similar to other openings, e.g., opening 412, previously described herein. Spring arm section 514 is dimensioned to house a cam pin 504. In the embodiment illustrated in FIG. 4A, spring arm section 514 is proportionally larger than upright section 512 (see FIG. 4A). More particularly, upright section 512 includes a width that is smaller than a width of the spring arm section 514. The smaller width of the upright section 512 facilitates flexing or pivoting the spring arm section 514 at a distal tip 518 of the upright section 512 when cam pin 504 is moved proximally within the spring arm section 514.

In an alternate embodiment jaw insert 500 includes an opening 520 of suitable dimensions, see FIG. 4B, for example. Opening 520 is defined by proximal and distal sidewalls 522 and 524, respectively, and upper and lower walls 526 and 528, respectively. A resilient of spring structure 530 of suitable proportion is operably associated with the jaw insert 500. More particularly, spring structure 530 is monolithically formed, i.e., molded, with the jaw insert 500. Alternatively, spring structure 530 may be a separate component, e.g., coil spring 350, leaf spring 360 and torsion spring 370, that is operably coupled to the jaw insert 500 by methods previously described herein. Spring structure 530 extends from a bottom wall 528 of the jaw insert 500. More particularly, spring structure 530 includes a generally elongated upright portion 532 that extends in a generally orthogonal orientation from bottom wall 528 toward top wall 526. Upright portion 532 includes an arcuate or concave section 534 that supports an elongated cam slot 536 dimensioned to house a cam pin 538 and configured to move the jaw member 110. This configuration of an upright portion 532 that includes an arcuate of concave section 534 facilitates flexing or pivoting the elongated cam slot 536 when cam pin 538 is moved proximally within the elongated cam slot 536. Cam pin 538 is configured and operates similar to other previously described cam pins, e.g., cam pin 504.

In an alternate embodiment, jaw insert 500 includes an opening 540 configured to house one or more resilient or spring-like structures 542 and a movable member 544 that includes a cam slot 546. Movable member 544 including cam slot 546 is configured identically to that of the previously described movable member 304 including cam slot 306 and, as a result thereof, will not be described in further detail. In the embodiment illustrated in FIG. 4C, spring-like structures 542 are in the form of two resilient fingers 548 and 550. More particularly, each of the fingers 548 and 550 is monolithically formed, i.e., molded, with the jaw insert 500. Finger 548 includes a generally arcuate configuration and extends from a proximal wall 552 of the jaw insert 500 to a proximal end 554 of the movable member 544. Likewise, finger 550 includes a generally arcuate configuration and extends from proximal sidewall 552 of the jaw insert 500 to a proximal end 554 of the movable member 544.

Operation of the forceps 10 with jaw insert 500 that includes a monolithically formed resilient or spring-like structure is identical to the operation of a forceps 10 that includes a spring depicted in any of the FIGS. 3A-3D. As a result thereof, operation of forceps 10 with jaw insert 500 is not described.

With reference now to FIG. 5 an alternate embodiment of the jaw insert 200 is shown and designated jaw insert 600. Jaw insert 600 is similar to the previously described jaw inserts, e.g., jaw insert 200. So as not to obscure the present disclosure with redundant information, only those operative features and components that are unique to jaw insert 600 are described. In the embodiment illustrated in FIG. 5, jaw insert 600 is described in terms of use with each of the jaw members 110 and 120. In the embodiment illustrated in FIG. 5, jaw members 110 and 120 function in a manner as described above with respect to jaw inserts 200 and 400. Accordingly, only those features and operative components associated with jaw members 110 and 120 that are necessary to facilitate understanding of the operative components associated with jaw insert 600 is described.

Jaw insert 600 includes a cam slot 602 configured to house a cam pin 604 that is movable within the cam slot 602. Unlike previously described cam slots, e.g., cam slot 306, cam slot 602 is positioned adjacent a proximal end 606 of the jaw insert 600. More particularly, cam slot 602 is set back closer to the proximal end 606 than a resilient member operably associated with the jaw insert 600. An opening 608 extends through the jaw insert 600 and is configured to receive a pivot pin 611 (opening 608 is shown engaged with pivot pin 611 and as such not explicitly visible). In the embodiment, illustrated in FIG. 5, a portion of the pivot pin 611 is dimensioned to securely house a portion of a resilient member 610 that is operably associated with the jaw insert 600. In one particular embodiment, opening 608 and/or the pivot pin housed therein includes a generally circumferential configuration.

A resilient member 610 in the form of a torsion spring 610 is operably associated with the jaw insert 600 and operably couples to each of the jaw members 110 and 120. More particularly, a proximal end 612 of suitable proportion and having a generally circumferential configuration is dimensioned to securely couple to the pivot pin 611. Two generally elongated fingers 614 and 616 extend from proximal end 612 adjacent the proximal ends of the jaw members, e.g., proximal end 117*b* of jaw member 110 and a proximal end 127*b* of the jaw member 120 (see FIG. 3D, for example), and fixedly couple to a respective distal end of the jaw member, e.g., distal end 117*a* of jaw member 117 and a distal end 127*a* of the jaw member 120. In the embodiment illustrated in FIG. 5, the torsion spring 610 biases the jaw members 110 and 120 toward each other to a closed position.

In use, initially jaw members 110 and 120 are biased in a closed position under the closure and/or sealing force provided by the torsion spring 610. Proximal movement of movable handle 40 causes the drive rod 150 to move proximally. Proximal movement of the drive rod 150 causes cam pin 604 positioned within the cam slot 602 to move proximally against the bias of the torsion spring 610, which, in turn, causes one or both of the jaw members, e.g., jaw member 120 to move away from the other jaw member, e.g., jaw member 110, such that tissue is may be positioned between the jaw members 110 and 120. Once tissue is positioned between the jaw members 110 and 120 the movable handle 40 is released, which, in turn, causes jaw member 120 to move toward jaw member 110 under the biasing force of the torsion spring 610 (e.g., a position when the jaw members 110 and 120 are in the closed or clamped position) generate a sealing or closure force at the jaw members 110 and 120. Thereafter, the previously described steps with respect to jaw inserts previously described, e.g., jaw inserts 200 and 300, may be carried out and the previously described effects to tissue with the same mechanical advantages (e.g., closure and/or sealing force at the jaw members 110 and 120) is achieved.

With reference now to FIG. 6 an alternate embodiment of a jaw insert 700 is shown. Jaw insert 700 is similar to the previously described jaw inserts, e.g., jaw insert 400. So as not to obscure the present disclosure with redundant information, only those operative features and components that are unique to jaw insert 700 are described. In the embodiment illustrated in FIG. 6, jaw insert 700 is described in terms of use with the jaw member 110. In the embodiment illustrated in FIG. 6, jaw member 110 functions in a manner as described above with respect to jaw inserts 200. Accordingly, only those features and operative components associated with jaw member 110 that are necessary to facilitate understanding of the operative components associated with jaw insert 700 is described.

Jaw insert 700 includes a cam slot 702 configured to house a cam pin 704 that is movable within the cam slot 702. Similar to the cam slot 410 of jaw insert 400, cam slot 702 is orientated in a direction that is substantially parallel, i.e., horizontal, to the longitudinal axis "A-A." Cam slot 702 is in substantial alignment with an opening 706, which is configured in a manner similar to previously described openings, e.g., opening 212 that houses a pivot pin 708 (opening 706 is shown engaged with pivot pin 708 and as such not explicitly visible). In an alternate embodiment cam slot 702 may be angled (e.g., see cam slot 306 in FIGS. 3A-3C) or curved.

A resilient member 710 in the form of a spring loaded link 710 is operably associated with the jaw insert 700 and operably couples to the cam pin 704. More particularly, a proximal end 712 of the spring loaded link 710 operably couples to a proximal end 722 of the jaw insert 700 adjacent an upper portion of the jaw insert 700, and a distal end 714 of the spring loaded link 710 operably couples to the cam pin 704 forming a "crank-like" mechanical relationship.

One or more types of springs may be utilized to form a spring component 713 of the spring loaded link 710. For example, one type of spring that may be utilized to form a spring component 713 of the spring loaded link 710 may be a stamped spring 716, see FIG. 7A. Alternatively, a torsion spring 718 may be utilized to form a spring component of the spring loaded link 710, see FIG. 7B. The springs illustrated in FIGS. 7A and 7B are two of many springs that me be utilized to form spring component 713 of the spring loaded link 710.

In one particular embodiment, a limit band 720 may operably couple to the spring component 713, e.g., stamped spring 716 (see FIG. 7A, for example). In this instance, the limit band 720 limits the amount of deflection associated with the spring 716. In one particular embodiment, the limiting band 720 functions as a latching device. More particularly, the limit band 720 functions to maintain the jaw members 110 and 120 in a substantially fixed position, e.g., a closed or clamped position. In one particular embodiment, after tissue has been treated, e.g., sealed, a rigid or strong pushing force unlatches the limit band 720 such that the cam pin 704 is allowed to move within the cam slot 702, whereby one or both of the jaw members 110 and 120 is allowed to move from the closed to the open position. Moreover, a preload on the limit band 720 and/or spring 713 may be configured to help tolerances and deflection length.

Operation of a forceps 10 that includes jaw insert 700 with a spring loaded link 710 is substantially similar to the operation of a forceps 10 that includes jaw insert 300. More particularly, when the cam pin 704 is moved. i.e., "pulled," to a set position, e.g., position when the jaw members 110 and 120 are in the closed or clamped position, the biased cam pin 704 generates a sealing or closure force at the jaw members 110 and 120. In the instance where a limit band 720 is utilized, the limit band 720 limits the amount of deflection that may be achieved by the spring 716 and/or locks or latches the jaw members 110 and 120 in a substantially fixed position, e.g., closed or clamped position. Thereafter, the previously described steps with respect to jaw insert 300 may be carried out with an additional step of unlatching the limit band 720 such that the jaw members 110 and 120 may return to the initial open position. The combination of jaw insert 700 including a spring loaded link 710 provides a consistent, uniform tissue effect, e.g., tissue seal, and an electrical insulation barrier between the seal plates 118, 128 and one or more of the operative components described above with respect to jaw insert 700. The combination of jaw insert 700 including a spring loaded link 710 may provide an additional mechanical advantage when employed with surgical devices with small jaws, such as, for example, flexible catheters that employ small jaws configured for jaw insertion into surgical ports of relatively small dimension.

From the foregoing and with reference to the various figure drawings, those skilled in the art will appreciate that certain modifications can also be made to the present disclosure without departing from the scope of the same. For example, other spring mechanisms such as, for example, foam, spring washers, bellows and compressed air and so forth, may be operably associated with any of the aforementioned jaw inserts, e.g., jaw insert 300, and utilized to generate a closure or sealing force at the jaw members.

It is contemplated that any of the aforementioned jaw inserts, e.g., jaw insert 300, may be made from a conductive material and utilized to provide the necessary closure force or a portion thereof to the first and second jaw members 110 and 120, respectively.

Figure 8:
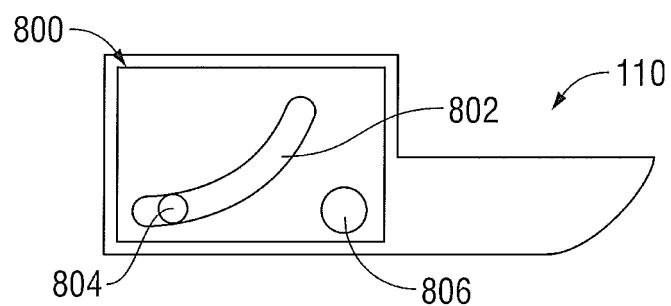
FIG. 8 is a schematic view of a jaw member including a jaw insert according to still another embodiment of the present disclosure.

An embodiment of a jaw insert in accordance with the present disclosure is illustrated in FIG. 8 and is designated jaw insert 800. Jaw insert 800 may include a cam slot 802 that is angled, arcuate, curved or otherwise shaped to provide a desired range of motion when the respective jaw members 110 and 120 are moving from the open position to the clamping position and a desired closure and/or sealing force when the respective first and second jaw members 110 and 120 are in a closed or clamping position. A cam pin 804 is operably disposed within the cam slot 802. An opening 806 is configured to receive a corresponding pivot pin, e.g., pivot pin 211. A distinguishing feature of opening 806 when compared to previously described openings, e.g., openings 608 and 708, is that opening 806 is positioned adjacent a bottom portion of the jaw insert 800 and distal with respect to the cam slot 802. Positioning the opening adjacent the bottom portion of the insert 800 facilitates obtaining a desired range of motion of the jaw member 110 and/or the jaw member 120.

Figure 9:
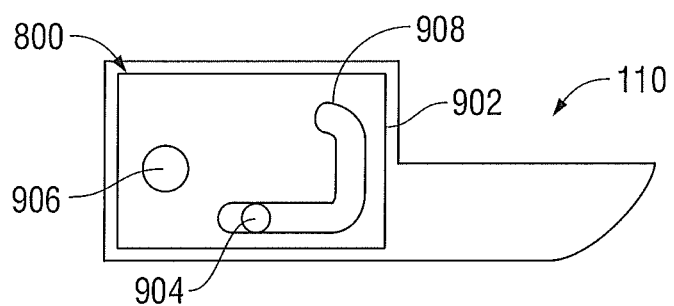
FIG. 9 is a schematic view of a jaw member including a jaw insert according to yet another embodiment of the present disclosure.

An embodiment of a jaw insert in accordance with the present disclosure is illustrated in FIG. 9 and is designated jaw insert 900. Jaw insert 900 may include a cam slot 902 that is angled, arcuate, curved or otherwise shaped (e.g., generally "j" shaped) to provide a desired range of motion when the respective jaw members 110 and 120 are moving from the open position to the clamping position and a desired closure and/or sealing force when the respective first and second jaw members 110 and 120 are in a closed or clamping position. In the embodiment illustrated in FIG. 9, a portion 908 of the cam slot 902 may extend back toward a proximal end of the jaw member 110. In this instance, portion 908 extends back toward the proximal end of the jaw member 110 and provides additional closure or sealing force (or range of motion of the first and second jaw members) when the respective first and second jaw members 110 and 120 are in a closed or clamping position. A cam pin 904 is operably disposed within the cam slot 902. An opening 906 is configured to receive a corresponding pivot pin, e.g., pivot pin 211. A distinguishing feature of opening 906 when compared to previously described openings, e.g., openings 608, 708 and 806, is that opening 906 is positioned adjacent a proximal end of the jaw insert 900 and proximal with respect to the cam slot 902. Positioning the opening adjacent the proximal end of the insert 800 facilitates obtaining a desired range of motion of the first jaw member 110 and/or the second jaw member 120.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    a housing;
    at least one shaft extending from the housing, the at least one shaft defining a longitudinal axis;
    an end effector assembly operatively connected to a distal end of the at least one shaft having first and second jaw members, the first and second jaw members movable relative to one another from an open position wherein the first and second jaw members are disposed in spaced relation relative to one another, to a clamping position wherein the first and second jaw members cooperate to grasp tissue therebetween; and
    a jaw insert operably disposed within at least one of the first and second jaw members, the jaw insert defining an opening configured to securely house a pivot pin, the pivot pin providing an axis of pivot for the first and second jaw members, the jaw insert including a moveable member defining a cam slot, the cam slot configured to receive a cam pin that upon movement of the cam pin rotates the jaw members from the open position to the clamping position, the moveable member configured to provide a camming force to the cam slot and a portion of a sealing force to the jaw members when the first and second jaw members are in the clamping position.

2. The forceps of claim 1, wherein the moveable member is operably associated with a spring.

3. The forceps of claim 2, wherein the spring is disposed within the jaw insert.

4. The forceps of claim 3, wherein the spring is positioned between a proximal wall of the jaw insert and a proximal end of the movable member.

5. The forceps of claim 2, wherein the type of spring is selected from the group consisting of a torsion spring, a leaf spring, and a coil spring.

6. The forceps of claim 2, wherein the moveable member defines a spring opening sized and configured to receive the spring.

7. The forceps of claim 2, wherein a limit band is operably coupled to the spring and is configured to limit movement of the spring.

8. The forceps of claim 2, wherein the spring is rated less than 120 pounds per square inch.

9. The forceps of claim 1, wherein the moveable member includes a groove slidably engaged to a corresponding detent of the jaw insert, the groove configured to maintain the moveable member in substantial alignment with the longitudinal axis.

10. The forceps of claim 1, wherein the moveable member includes a detent slidably engaged within a corresponding groove of the jaw insert, the detent configured to maintain the moveable member in substantial alignment with the longitudinal axis.

11. The forceps of claim 1, wherein the cam slot is disposed at an angle relative to the longitudinal axis.

12. The forceps of claim 1, wherein the jaw insert is manufactured from an insulative medium to dielectrically isolate the first and second jaw members and the jaw insert is overmolded to at least one of the first and second jaw members.

13. The forceps of claim 1, wherein the opening is positioned at a distal location relative to the cam slot.

* * * * *